United States Patent
Gürtler et al.

(10) Patent No.: US 6,756,500 B1
(45) Date of Patent: Jun. 29, 2004

(54) α,ω-DIENE METATHESIS IN THE PRESENCE OF IONIC LIQUIDS

(75) Inventors: Christoph Gürtler, Köln (DE); Manfred Jautelat, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/514,023

(22) Filed: Feb. 25, 2000

(30) Foreign Application Priority Data

Mar. 5, 1999 (DE) ......................................... 199 09 600
Jun. 18, 1999 (DE) ......................................... 199 27 912

(51) Int. Cl.[7] .................... C07D 209/48; C07D 209/00; C07D 231/00; C07D 269/00; C07D 303/00
(52) U.S. Cl. ........................ 548/480; 560/115; 564/12; 564/57; 564/84; 564/217; 564/444
(58) Field of Search ................................. 502/103, 152, 502/155, 156; 556/58, 136; 540/451; 548/531, 480; 549/472; 560/128, 115; 585/366, 367

(56) References Cited

U.S. PATENT DOCUMENTS

| | | | |
|---|---|---|---|
| 5,104,840 A | 4/1992 | Chauvin et al. | ............ 502/117 |
| 5,110,885 A | 5/1992 | Wagener et al. | ............ 526/170 |
| 5,312,940 A | 5/1994 | Grubbs et al. | ............... 556/136 |
| 5,525,567 A | 6/1996 | Chauvin et al. | ............ 502/162 |
| 6,235,925 B1 * | 5/2001 | Gurtler et al. | ............... 560/115 |

FOREIGN PATENT DOCUMENTS

| | | |
|---|---|---|
| EP | 882 691 | 12/1998 |
| WO | 96/04289 | 2/1996 |

OTHER PUBLICATIONS

Collmann, J.P. et al, "Principles and Applications of Organotransition Metal Chemistry", 1980, University Science Books, Mill Valley, CA, p. 49.*
Campagne, J.–M. et al, Tet. Lett., 39, 1998, 6175–6178.*
Armstrong, S. K., J. Chem. Soc., Perkin I, 1998, 371–388.*
Olivier, Helene; Chauvin, Yves, Chem. Ind. (Dekker) (1996), 68(Catalysis of Organic Reactions), 249–263.*
Buijsman, Rogier C.; van Vuuren, Elizabeth; Sterrenburg, Jan Gerard, Organic Letters (2001), 3(23), 3785–3787.*
Olivier et al Chemistry in Industry 68 (1996) 249–263.*
M. Schuster, S. Blechert, Angew. Chem. 109, (month unavailable) 1997, pp. 2124–2144 Die Olefinmetathese in der organischen Synthese.
S. Armstrong, J. Chem. Soc. Perkin Trans. 1 (month unavailable) 1998, pp. 371–388 Ring closing diene metathesis in organic synthesis.
O. Brümmer et al., Chem. Eur. J. 3, (month unavailable) 1997, pp. 441–446, Olefin Cross–Metathesis with Mono-substituted Olefins.
A.W. Stumpf et al, J. Chem. Soc. Chem. Commun. (month unavailable) 1995, pp. 1127–1128 Ruthenium–based Catalysts for the Ring Opening Metathesis Polymerisation of Low–strain Cyclic Olefins and of Funtionalised Derivatives of Norobornene and Cyclooctene.
P. Schwab, et al, J. Am. Chem. Soc. (mont unavailable) 1996, pp. 118–110, Synthesis and Applications of RuCl$_2$(=CHR')(PR$_3$)$_2$: The Influence of the Alkylidene Moiety on Metathesis Activity.
Journals of the Chemical Society, Perkin Transactions 1, (month unavailable), 1998, Seiten 371–388, XP002153812, Letchworht GB, Seite 381, Spalte 2, Seite 382, Spalte 2, S. K. Armstrong "Ring Closing Diene Metathesis in Organic Synthesis".

* cited by examiner

Primary Examiner—James O. Wilson
Assistant Examiner—Thomas McKenzie
(74) Attorney, Agent, or Firm—Godifled E. Akorjt; Diderico van Eyl

(57) ABSTRACT

A process for preparing a cyclic compound comprising subjecting a starting material in the presence of a catalyst component to metathesis reaction in the presence of an ionic liquid, wherein the starting material is a α,ω-diene bearing a α substituent $NRR^1$ in the α position to a double bond, wherein R is hydrogen or an organic substituent, $R^1$ is tert-butyl, $P(R)_2$, $P(R^2)_2$, COR, $SO_2PhR$, COOR or $CONRR^2$, $R^2$ is alkyl or phenyl, or R and $R^1$ together form

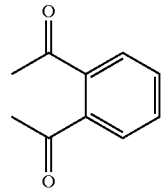

and in which α,ω-dienes optionally bear at least one further substituent R in any other position with the exception of the α position, wherein R is selected from the group consisting of hydrogen, fused or unfused aryl, alkyl, CN, $COOR^2$ or halogen, and wherein the starting material optionally contains a member selected from the group containing at least one further substituent that is inert in the metathesis reaction and a heteroatom selected from the group consisting of branched alkyl radicals, unbranched alkyl radicals, aromatic carbocyclic rings, non-aromatic carbocyclic rings, carboxylic acids, esters, ethers, epoxides, silyl ethers, thioethers, thioacetals, anhydrides, imines, silylenol ethers, ammonium salts, amides, nitriles, perfluoroalkyl groups, geminal dialkyl groups, alkynes, alkenes, halogens, alcohols, ketones, aldehydes, carbamates, carbonates, urethanes, sulfonates, sulfones, sulfonamides, nitro groups, organosilane units, metal centers and oxygen-containing heterocycles, nitrogen-containing heterocycles, sulfur-containing heterocycles and phosphorus-containing heterocycles, wherein the catalyst component includes homogeneous catalysts and heterogeneous catalysts selected from the group consisting of (i) transition metal carbenes, (ii) transition metal compounds that form transition metal carbenes under the reaction conditions, and (iii) transition metal salts in combination with an alkylating agent.

12 Claims, No Drawings

α,ω-DIENE METATHESIS IN THE PRESENCE OF IONIC LIQUIDS

BACKGROUND OF THE INVENTION

The present invention relates to a process for preparing cyclic and/or polymeric compounds by metathesis of starting materials that contain at least two functional groups in the form of substituted or unsubstituted alkene or alkyne units.

For the purposes of the present invention, the term "metathesis" refers to a mutual transalkylidenation of alkenes and alkynes in the presence of catalysts. Reactions of this type are employed in many industrially important processes. A review may be found in: M. Schuster, S. Blechert, Angew. Chem. 1997, 109, 2124 and S. Armstrong, J. Chem. Soc., Perkin Trans. 1, 1998, 371. Metathesis reactions include the oligomerization and polymerization of acyclic dienes (ADMET) and the synthesis of carbocycles and heterocycles having various ring sizes by ring closing metathesis (RCM). Crossed metatheses of different alkenes are also known (Brümmer, O. et al. Chem. Eur. J. 1997, 3, 441).

For the above-mentioned metathesis reactions, it is possible to use the ruthenium-alkylidene compounds described in WO-A-93/20111, the ruthenium-based catalyst systems described by A. W. Stumpf, E. Saive, A. Deomceau and A. F. Noels in J. Chem. Soc., Chem. Commun. 1995, 1127–1128, or the catalyst systems described by P. Schwab, R. H. Grubbs and J. W. Ziller in J. Am. Chem. Soc. 1996, 118, 100 (see also WO 96/04289) as catalysts.

The use of nonaqueous ionic liquids for metathesis reactions has recently been described. These ionic liquids are salts or mixtures of salts that are liquid over a wide temperature range. The advantage of ionic liquids is that they are immiscible with aliphatic hydrocarbons. In organic reactions for which the use of a catalyst is necessary, heterogeneous catalysis can be achieved by addition of ionic liquids and a suitable catalyst that dissolves only or preferentially in the ionic liquid.

U.S. Pat. No. 5,104,840 describes the use of such mixtures as solvents for transition metal complexes, especially nickel complexes that contain no carbon-nickel bonds.

EP-B-448445 describes the use of ionic liquids for the dimerization of unsubstituted monoolefins using nickel chloride. However, a disadvantage here is the use of organoaluminium halide, especially the pyrophoric dichloroethylaluminium, for preparing the ionic liquid.

U.S. Pat. No. 5,525,567 describes the use of ionic liquids for the disproportionation of unsubstituted monoolefins using tungsten catalysts. Here too, it is necessary to use an organoaluminium halide, preferably the pyrophoric dichloroethylaluminium, for preparing the ionic liquid.

EP-A-882691 describes the use of ionic liquids for the dimerization of unsubstituted monoolefins in the presence of nickel chloride. Apart from the pyrophoric dichloroethylaluminium that is used here too, a further disadvantage is that the excess of the Lewis acid aluminium chloride in the ionic liquid results in an acidic reaction mixture.

The above-described metathesis processes are, moreover, suitable only for the reaction of unsubstituted monoolefins, i.e. very simple organic molecules. These processes are not suitable for the reaction of multiply substituted starting materials bearing functional groups, since the catalysts described there cannot be employed or the ionic liquids are unsuitable for other catalysts because of their composition or the fact that the reaction mixture has an acidic character.

It is an object of the present invention to provide a universally usable process for the metathesis of starting materials that contain at least two functional groups in the form of alkene or alkyne units that is carried out using ionic liquids. The process should also be able to be used for substituted alkenes or alkynes.

SUMMARY OF THE INVENTION

The invention, meeting the above-named object, provides a process that subjects starting materials that contain at least two functional groups in the form of alkene or alkyne units to metathesis. The process is carried out using ionic liquids. Advantageously, the process can be used for substituted alkenes or alkynes. These and other features, aspects, and advantages of the present invention will become better understood with reference to the following description and appended claims.

DESCRIPTION OF THE INVENTION

We have found a process for preparing cyclic and/or polymeric compounds by metathesis of starting materials that contain at least two functional groups in the form of substituted or unsubstituted alkene or alkyne units in the presence of one or more homogeneous or heterogeneous catalysts, wherein the metathesis is carried out in the presence of ionic liquids and the catalysts used are transition metal carbenes or transition metal compounds that form transition metal carbenes under the reaction conditions or transition metal salts in combination with an alkylating agent.

It has surprisingly been found that the presence of ionic liquids in the metathesis reaction of starting materials that contain at least two functional groups in the form of substituted or unsubstituted alkene or alkyne units leads to an increase in the operating life of the catalyst since it can be used in the ionic liquid for further metathesis reactions.

In a preferred embodiment, the present invention makes it possible to prepare carbocyclic or heterocyclic compounds having ring sizes of $\geq 5$ ring atoms, including medium-sized rings (from 8 to 11 ring atoms) and large rings ($\geq 12$ ring atoms) and/or polymeric compounds that can be homopolymers, copolymers or block copolymers.

In ring closing metathesis reactions, the ring-closure reaction competes with polymerization. If this reaction is carried out using starting materials that contain at least two functional groups in the form of alkene or alkyne units, it results in mixtures of cyclic compounds and polymers.

The formation of cyclic compounds is favoured by carrying out the reaction in organic solvents at high dilution or by addition of relatively large volumes of ionic liquids. This applies particularly to the preparation of medium-sized rings (from 8 to 11 ring atoms) and large rings ($\geq 12$ ring atoms).

The large reaction volumes of organic solvents required to achieve the necessary high dilution limit the maximum space-time yields. Separating off the products after the reaction is complete requires time-consuming separation operations such as chromatography and usually leads to irreversible deactivation of the catalyst used.

The use of relatively large volumes of ionic liquids does, however, allow the desired products to be separated off easily, since they are present in the organic phase that is not miscible with the ionic liquid. If a catalyst that dissolves exclusively or preferentially in the ionic liquid is selected, the deactivation of the catalyst after the work-up can be avoided and the phase comprising the ionic liquid and the catalyst can be used for further metathesis reactions.

In the process of the invention, preference is given to using starting materials that contain, apart from the functional groups participating in the metathesis reaction, at least one further substituent that is inert in the metathesis reaction and/or a heteroatom. These substituents or heteroatoms can be selected independently from among: branched or unbranched alkyl radicals, aromatic or nonaromatic carbocyclic rings, carboxylic acids, esters, ethers, epoxides, silyl ethers, thioethers, thioacetals, anhydrides, imines, silylenol ethers, ammonium salts, amides, nitriles, perfluoroalkyl groups, geminal dialkyl groups, alkynes, alkenes, halogens, alcohols, ketones, aldehydes, carbamates, carbonates, urethanes, sulphonates, sulphones, sulphonamides, nitro groups, organosilane units, metal centres and oxygen, nitrogen, sulphur and/or phosphorus-containing heterocycles.

The process of the invention is particularly preferably carried out using, as starting materials, $\alpha,\omega$-dienes that may contain at least one further substituent that is inert in the metathesis reaction and/or a heteroatom. These substituents or heteroatoms may be selected independently from among branched or unbranched alkyl radicals, aromatic or nonaromatic carbocyclic rings, carboxylic acids, esters, ethers, epoxides, silyl ethers, thioethers, thioacetals, anhydrides, imines, silylenol ethers, ammonium salts, amides, nitrites, perfluoroalkyl groups, geminal dialkyl groups, alkynes, alkenes, halogens, alcohols, ketones, aldehydes, carbamates, carbonates, urethanes, sulphonates, sulphones, sulphonamides, nitro groups, organosilane units, metal centres and oxygen-, nitrogen-, sulphur- and/or phosphorus-containing heterocycles.

In particular, the process of the invention is carried out using, as starting materials, $\alpha,\omega$-dienes that bear a substituent $NRR^1$ in the $\alpha$ position to a double bond, wherein R is an organic substituent, preferably hydrogen, fused or unfused aryl, alkyl, CN, $COOR^2$ or halogen, $R^1$ is tert-butyl, $P(R)_2$, $P(R^2)_2$, COR, $SO_2PhR$, COOR or $CONRR^2$, $R^2$ is alkyl or phenyl, R and $R^1$ together form

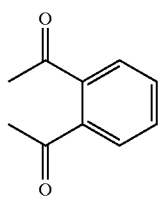

and said $\alpha,\omega$-dienes may also bear at least one further substituent R in any other position in the molecule with the exception of the $\alpha$ position. Use of these dienes as starting materials in the process of the invention makes it possible to obtain cyclic and/or polymeric compounds that bear a substituent $NRR^1$, wherein R and $R^1$ are as defined above, in the $\alpha$ position to the double bond.

In a particularly preferred embodiment, the above-mentioned $\alpha,\omega$-dienes are compounds of the formula (I)

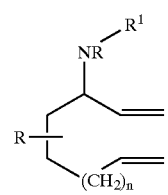

(I)

wherein R, $R^1$ and $R^2$ are as defined above and n is 1, 2, 3 or 4, preferably 1 or 2, particularly preferably 1.

When using compounds of the formula (I), the process of the invention preferably gives cyclic compounds of the formula (II),

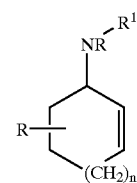

(II)

wherein R, $R^1$, $R^2$ and n are as defined above and the double bond may also be substituted by at least one radical R, and/or polymeric products.

Starting materials that are very particularly preferably used in the process of the invention are diallylamine or 3-amino-1,7-octadiene, particularly preferably in their N-carboxymethyl-protected form, or 1,7-octadiene, 10-undecenoyl-allylamide, 1,4-bis-oxypropen-2-yl-but-2-ine or buten-4-yl 10-undecenoate.

It is also possible to use mixtures of starting materials in the process of the invention. In this case, the starting materials can be added as a mixture to the reaction medium or else can be added sequentially to the reaction medium.

In the process of the invention, the catalysts or catalyst precursors used are transition metal carbenes or transition metal compounds that form transition metal carbenes under the reaction conditions or transition metal salts in combination with an alkylating agent. These catalysts can be either ionic or nonionic.

The process of the invention is preferably carried out using catalysts of the formulae (III) to (VI), wherein M is ruthenium or osmium, preferably ruthenium.

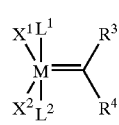

(III)

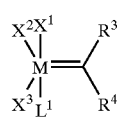

(IV)

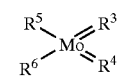

(V)

-continued

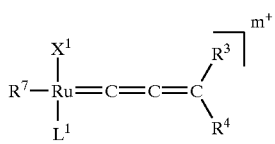
(VI)

$R^3$ to $R^7$ are radicals that can be selected independently from among hydrogen, $C_1$–$C_{20}$-alkyl, $C_3$–$C_8$-cycloalkyl, $C_2$–$C_{20}$-alkenyl, $C_2$–$C_{20}$-alkinyl, $C_6$–$C_{18}$-aryl, $C_1$–$C_{20}$-carboxylate, $C_1$–$C_{20}$-alkoxy, $C_2$–$C_{20}$-alkenyloxy, $C_2$–$C_{20}$-alkinyloxy, $C_8$–$C_{18}$-aryloxy, $C_2$–$C_{20}$-alkoxycarbonyl, $C_1$–$C_{20}$-alkylthio, $C_1$–$C_{20}$-alkylsulphonyl or $C_1$–$C_{20}$-alkylsulphinyl, N-aryl; in each case unsubstituted or substituted by $C_1$–$C_{12}$-alkyl, perfluoroalkyl, halogen, $C_1$–$C_5$-alkoxy or $C_6$–$C_{18}$-aryl. The radicals $R^3$ to $R^7$ may be linked to one another in cyclic compounds.

$X^1$ to $X^3$ are anionic ligands that may be selected independently, in particular $F^-$, $Cl^-$, $Br^-$, $CN^-$, $SCN^-$, $R^3O^-$, $R^3R^4N^-$, $(R^3$–$R^7)$-allyl$^-$, $(R^3$–$R^7)$-cyclopentadienyl$^-$, wherein the radicals $R^3$ to $R^7$ are as defined above.

$L^1$ to $L^3$ are uncharged ligands that can be selected independently, in particular CO, $CO_2$, $R^3NCO$, $R^3R^4C=CR^5R^6$, $R^3C\equiv CR^4$, $R^3R^4C=NR^5$, $R^3C\equiv N$, $R^3OR^4$, $R^3SR^4$, $NR^3R^4R^5$, $PR^3R^4R^5$, $AsR^3R^4R^5$, $SbR^3R^4R^5$, wherein the radicals $R^3$ to $R^5$ are as defined above;

m is 1 or 2.

Particularly preferred catalysts or catalyst precursors are compounds of the formulae (III) and (IV) in which $L^1$ and $L^2$=$PR^3R^4R^5$, where $R^3$ to $R^5$ are as defined above and very particularly preferred radicals of this type are aryl or alkyl, in particular secondary alkyl radicals or cycloalkyl radicals.

Very particular preference is given to using the following compounds as catalysts in the process of the invention:

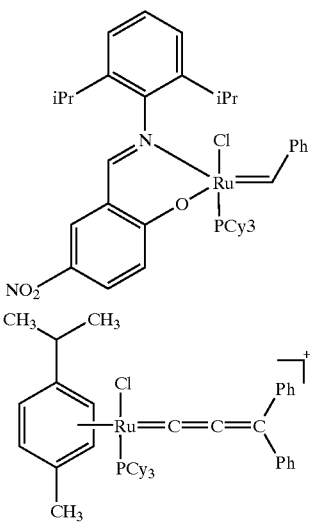

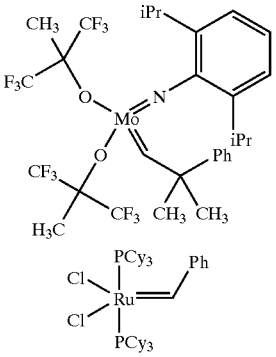

where Cy=cyclohexyl, iPr=isopropyl, Ph=phenyl.

The catalysts can be used in isolated form or can be generated in situ in the reaction medium from catalyst precursors. The amounts of catalyst that are used in the process of the invention are generally from 0.001 to 15 mol %, based on the starting materials. The process of the present invention is preferably carried out using from 0.1 to 12 mol % of catalyst, particularly preferably from 0.5 to 9 mol %, based on the starting materials.

The ionic liquids used in the process of the invention are salts or salt mixtures that are liquid in a temperature range from −20° C. to 300° C.

In the process of the invention, preference is given to using ionic liquids that comprise aluminium halides in combination with at least one quaternary ammonium halide and/or at least one quaternary phosphonium halide.

As quaternary ammonium compounds, particular preference is given to using heterocyclic compounds that contain at least one nitrogen atom. These are, for example, pyridinium compounds or imidazolium compounds.

Very particularly preferred ionic liquids are aluminium chloride in combination with 1-methyl-3-butylimidazolium chloride, 1-methyl-3-ethylimidazolium chloride, N-butylpyridinium chloride and/or tetrabutylphosphonium chloride.

The process of the invention is preferably carried out using ionic liquids that comprise a combination of aluminium halide and quaternary ammonium halides and/or quaternary phosphonium halides in a molar ratio of (0.6–1):1. The molar ratio of aluminium halide to quaternary ammonium halide and/or quaternary phosphonium halide should never be greater than 1 since otherwise an excess of Lewis acid is present in the reaction mixture. This acidic reaction mixture leads to deactivation of the transition metal carbene catalysts.

Preference is also given to using ionic liquids that comprise ammonium hexafluorophosphate, ammonium tetrafluoroborate, ammonium tosylate or ammonium hydrogen sulphate or consist of ammonium hexafluorophosphate, ammonium tetrafluoroborate, ammonium tosylate or ammonium hydrogen sulphate in the process of the invention.

Ionic liquids used are particularly preferably pyridinium hexafluoro-phosphate, 1-methyl-3-butyl hexafluorophosphate, pyridinium tetrafluoroborate, pyridinium hydrogen sulphate or N-butylpyridinium hexafluorophosphate.

As ionic liquids in the process of the invention, it is also possible to use combinations of aluminium halide with mixtures of quaternary ammonium halides and/or quaternary phosphonium halides, or mixtures of ammonium hexafluorophosphates, ammonium tetrafluoroborates, ammonium tosylates or ammonium hydrogen sulphates.

The process of the invention can be carried out in the presence of one or more additives, preferably a solvent, that, for example, makes it easier to separate the products from the ionic liquid and the catalyst present therein. In the presence of an additive and the ionic liquids, a heterogeneous catalyst system is obtained when ionic catalysts or catalysts that dissolve preferentially in the ionic liquid are used. After the metathesis reaction is complete, the ionic phase comprising the catalyst can easily be separated from the additive and the reaction product present therein. The catalyst in the ionic liquid can be used for further metathesis reactions without intermediate purification steps.

Such additives can be selected, for example, from among: phosphorus compounds, amines, perfluorinated compounds, metal alkoxides and organic solvents. Suitable organic solvents are, in particular, halogenated hydrocarbons such as dichloromethane, trichloromethane, tetrachloromethane, 1,2-dichloroethane or trichloroethane, aromatic compounds such as benzene, toluene, xylene, cumene or halogenobenzenes, alkanes such as pentane, hexane or cyclohexane, esters such as tert-butylmethyl esters or acetic esters, ethers such as diethyl ether, tetrahydrofuran and dimethoxyethane, amides such as dimethylformamide, antioxidants such as hydroquinones, acetone, dimethyl carbonate or alcohols.

Preferred additives for use in the process of the invention are $C_5$–$C_{20}$-alkanes, ethers and halogenated hydrocarbons.

Pentane, n-hexane, methyl tert-butyl ether or dichloromethane are very particularly preferably used in the process of the invention.

The process of the invention is preferably carried out at pressures in the range from 0.1 to 10 bar, particularly preferably at atmospheric pressure. However, the process of the invention can also be carried out at subatmospheric pressures down to 0.01 bar and superatmospheric pressures up to 100 bar.

The process of the invention is usually carried out in a temperature range from −20° C. to 200° C., preferably from 0° C. to 150° C., very particularly preferably from 20° C. to 100° C.

The cyclic compounds or polymers that can be prepared by the process of the invention can be further purified and processed with the aid of customary methods. The catalyst in the ionic liquid can be used for further metathesis reactions without intermediate purification steps.

The invention is further illustrated but is not intended to be limited by the following examples in which all parts and percentages are by weight unless otherwise specified.

EXAMPLES

The examples below describe metathesis reactions in the presence of ionic liquids (and additives) under preferred conditions. However, they in no way restrict the scope of the present invention. The abbreviation Cy represents cyclohexyl, Ph represents phenyl, iPr represents isopropyl and TfO represents triflate.

Example 1

Preparation of N-carboxymethyl-2,5-dihydropyrrole

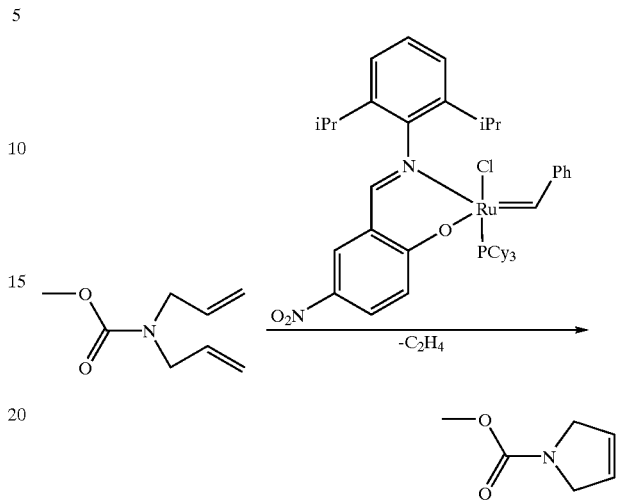

155 mg (1 mmol) of N-carboxymethyl-diallylamine and 17 mg of (tricyclo-hexylphosphine)-benzylidene-chloro-ruthenium(IV) 2-[(2,6diisopropyl-phenyl)imino]methyl-4-nitro-phenoxide (2 mol %) were dissolved in a liquid mixture of 579 mg of 1-methyl-3-ethylimidazolium chloride (4 mmol) and 533 mg of aluminum trichloride (4 mmol) under an argon atmosphere. The mixture was covered with 3 ml of absolute n-hexane. It was allowed to react for 30 minutes at room temperature while stirring. After phase separation, the ionic phase was washed three times with n-hexane.

Analysis of the organic phase by gas chromatography indicated a proportion of 30% of N-carboxymethyl-2,5-dihydropyrrole product. Covering the catalyst phase once more with a solution of 155 mg (1 mmol) of N-carboxymethyl-diallylamine in 3 ml of n-hexane, another reaction time of 30 minutes and an analogous work-up gave a yield of 20% of N-carboxymethyl-2,5-dihydropyrrole.

Example 2

Preparation of N-carboxymethyl-3,4,5,6-tetrahydroaniline

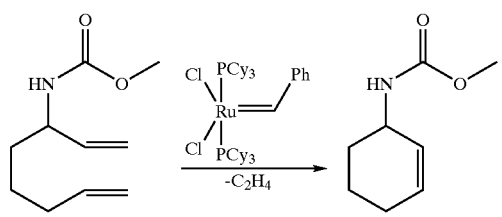

92 mg (0.5 mmol) of N-carboxymethyl-3-amino-1,7-octadiene and 4 mg of bis(tricyclohexylphosphine)-benzylidene-ruthenium(IV) dichloride (1 mol %) were dissolved in a liquid mixture of 586 mg of 1-methyl-3-ethylimidazolium chloride (4 mmol) and 533 mg of aluminium trichloride (4 mmol) under an argon atmosphere in a baked-out Schlenk tube. The mixture was allowed to react for two hours at 50° C. After an aqueous work-up, the mixture was filtered through a very short silica gel column (0.5 cm), washed four times with 1 ml each time of acetonitrile and evaporated.

Yield: 77 mg of N-carboxymethyl-3,4,5,6-tetrahydroaniline (0.49 mmol, 99% of theory).

$^1$H NMR (400 MHz, CDCl$_3$) 5.85 (1H, d, J=9.0 Hz), 5.60 (1H, d, J=9.0 Hz), 4.70 (1H, s), 4.20 (1H, s), 3.65 (3H, s), 1.98 (2H, m), 1.90 (1H, m), 1.62 (2H, m), 1.52 (1H, m).

Example 3

Preparation of N-carboxymethyl-3,4,5,6-tetrahydroaniline

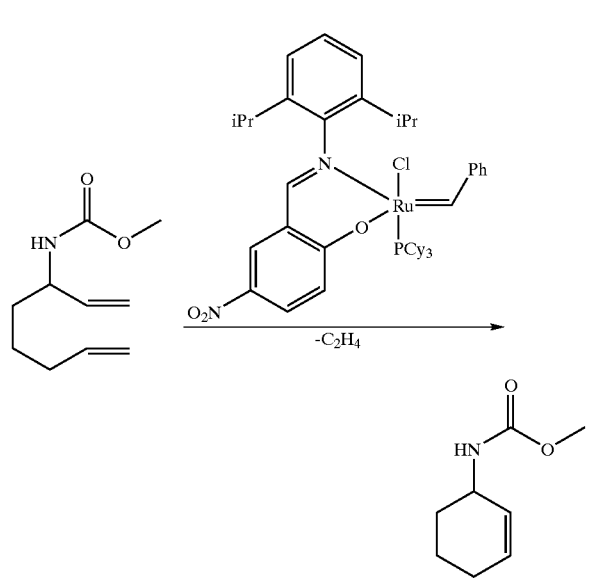

92 mg (0.5 mmol) of N-carboxymethyl-3-amino-1,7-octadiene and 10 mg of the ruthenium catalyst shown in the reaction scheme above, namely (tricyclohexylphosphine)-benzylidene-chloro-ruthenium-(IV) 2-[(2,6-diisopropyl-phenyl)imino]methyl-4-nitro-phenoxide, were dissolved in 1 ml of absolute hexane and a mixture of 290 mg (2 mmol) of 1-methyl-3-ethylimidazolium chloride and 266 mg (2 mmol) of aluminium trichloride under an argon atmosphere in a baked-out Schlenk tube. The mixture was allowed to react for 3 hours at 50° C. For the work-up, the organic phase was pipetted off and the phase comprising the ionic liquid was washed twice with 2 ml each time of hexane. The combined hexane phases were evaporated. Finally, the mixture was filtered through a very short silica gel column (0.2 cm), washed once with 1 ml of acetonitrile and evaporated. The catalyst dissolved in the ionic liquid is available for a further reaction with substrate in hexane.

Yield: 74 mg of N-carboxymethyl-3,4,5,6-tetrahydroaniline (0.48 mmol, 96% of theory).

Example 4

Preparation of N-carboxymethyl-3,4,5,6-tetrahydroaniline

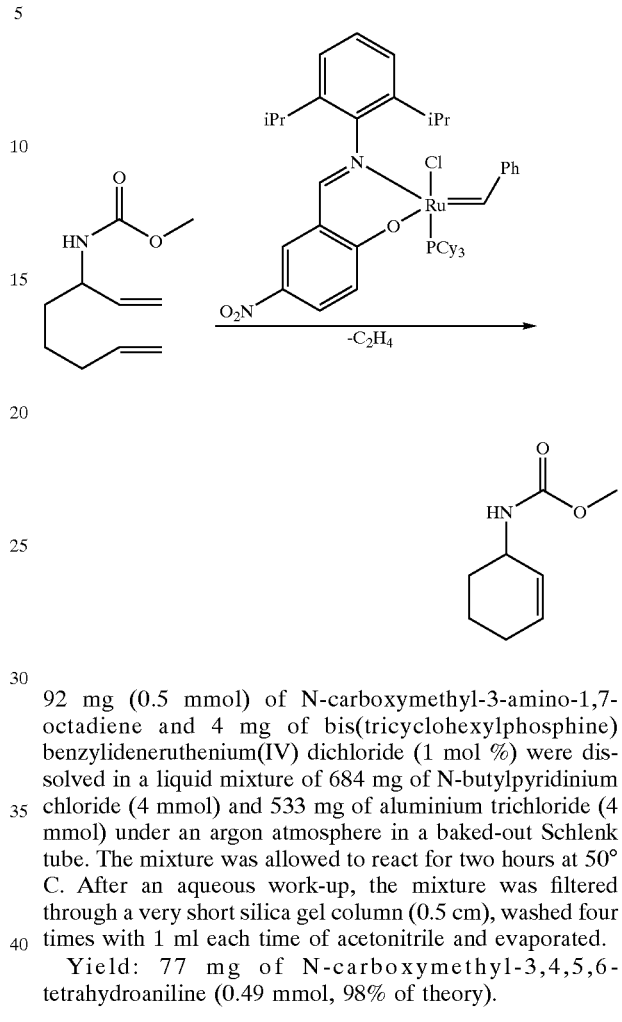

92 mg (0.5 mmol) of N-carboxymethyl-3-amino-1,7-octadiene and 4 mg of bis(tricyclohexylphosphine)benzylideneruthenium(IV) dichloride (1 mol %) were dissolved in a liquid mixture of 684 mg of N-butylpyridinium chloride (4 mmol) and 533 mg of aluminium trichloride (4 mmol) under an argon atmosphere in a baked-out Schlenk tube. The mixture was allowed to react for two hours at 50° C. After an aqueous work-up, the mixture was filtered through a very short silica gel column (0.5 cm), washed four times with 1 ml each time of acetonitrile and evaporated.

Yield: 77 mg of N-carboxymethyl-3,4,5,6-tetrahydroaniline (0.49 mmol, 98% of theory).

Example 5

Preparation of tetrahydrobenzene

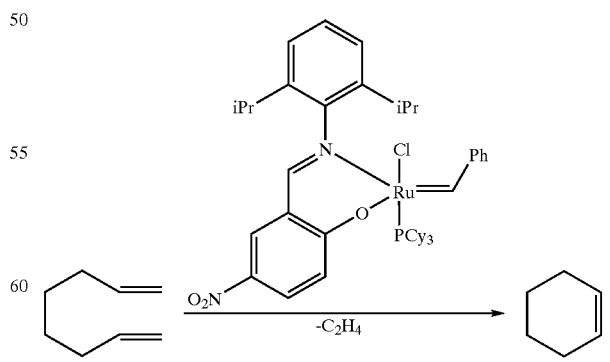

110 mg (1 mmol) of 1,7-octadiene and 17 mg of (tricyclohexylphosphine)-benzylidene-chloro-ruthenium-(IV) 2-[(2,6-diisopropylphenyl)imino]methyl-4-nitrophenoxide (2 mol %) were dissolved in 3 ml of absolute pentane under an argon atmosphere in a baked-out Schlenk tube. A liquid mixture of 579 mg of 1methyl-3-ethylimidazolium chloride (4 mmol) and 533 mg of aluminium trichloride (4 mmol) was added thereto. The mixture was allowed to react for 30 minutes at room temperature. For the work-up, the organic phase was pipetted off and the phase comprising the ionic liquid was washed twice with 2 ml each time of pentane. The combined pentane phases were evaporated. The mixture was subsequently filtered through a very short silica gel column (0.2 cm), washed once with 1 ml of pentane and evaporated.

The yield of tetrahydrobenzene was determined by gas chromatography (internal standard:tetradecane) and was 99% of theory.

After covering the reaction solution once more with a mixture of 110 mg (1 mmol) of 1,7-octadiene in pentane, a reaction time of 30 minutes and subsequent phase separation, a yield of 63% of tetrahydrobenzene was obtained.

Example 6

Preparation of tetrahydrobenzene

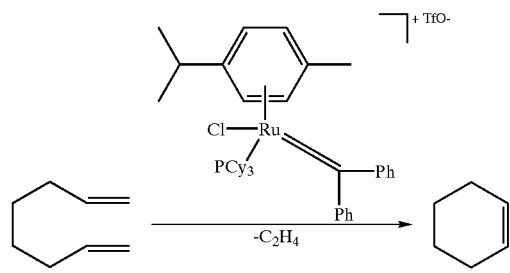

28 mg of 1,7-octadiene (0.25 mmol) were dissolved in a mixture of 345 mg (2 mmol) of 1-methyl-3-butylimidazolium chloride and 266 mg (2 mmol) of aluminium trichloride under an argon atmosphere in a 20 ml Schlenk tube. 11 mg of the cationic catalyst described in the reaction scheme above (5 mol %) were added thereto. The reaction solution was covered with 3 ml of methyl tert-butyl ether. The mixture was allowed to react for 90 minutes at a temperature of 40° C. and the organic phase was then separated off. The ionic phase was extracted three times with methyl tertbutyl ether. Gas chromatography found a content of 32% of the desired tetrahydro-benzene. This result was obtained again in a subsequent second metathesis reaction using the same ionic phase.

Example 7

Preparation of aminocyclotridec-11-en-2-one

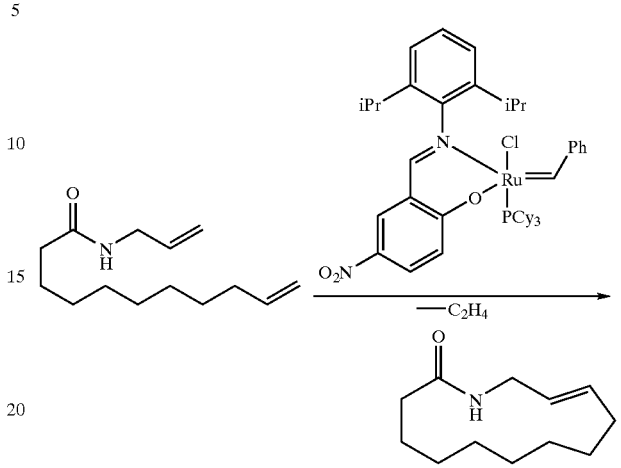

58 mg (0.25 mmol) of 10-undecenoyl-allylamide and 10 mg of (tricyclohexylphosphine)-benzylidene-chloro-ruthenium-(IV) 2-[(2,6-diisopropylphenyl)imino]methyl-4-nitrophenoxide (5 mol %) were dissolved in 3 g of 1-methyl-3-butylimidazolium hexafluorophosphate. The mixture was allowed to react at 40° C. for 14 hours. The ionic phase was extracted with dichloromethane. After filtration through a very short silica gel column (length about 0.5 cm), about 80% of the desired product were obtained (yield determined by means of gas chromatography). The trans/cis ratio of the product is about 5:1.

Example 8

Metathesis of buten-4-yl 10-undecenoate

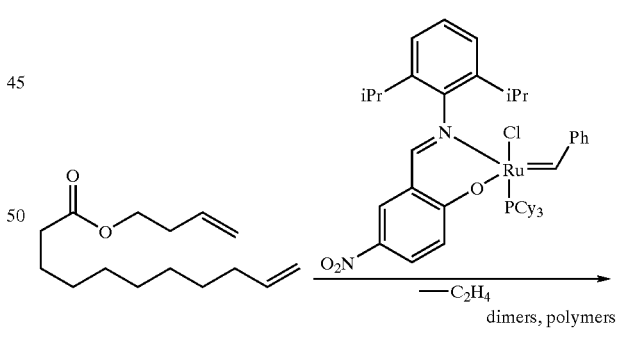

238 mg of buten-4-yl 10-undecenoate and 8 mg of (tricyclohexylphosphine)-benzylidene-chloro-ruthenium-(IV) 2-[(2,6-diisopropylphenyl)imino]methyl-4-nitrophenoxide (8 mol %) were dissolved in a mixture of 580 mg (4 mmol) of 1-methyl-3-ethylimidazolium chloride and 533 mg of aluminium trichloride (4 mmol). The mixture was covered with 40 ml of absolute pentane. It was allowed to react for five hours at room temperature while mixing well. Apart from a large percentage of polymer, about 10% of dimers of the diene used were obtained.

Example 9

Preparation of 3,3'-bis-2,5-dihydrofuranyl

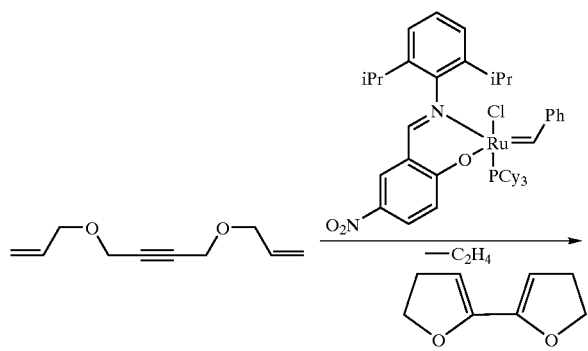

166 mg of 1,4-bis-oxypropen-2-yl-but-2-ine together with 41 mg of (tricyclohexylphosphine)-benzylidene-chloro-ruthenium-(IV) 2-[(2,6-diisopropylphenyl)imino]methyl-4-nitrophenoxide (5 mol %) were dissolved in a liquid mixture of 2.31 g of 1-methyl-3-ethylimidazolium chloride (16 mmol) and 2.13 g of aluminium trichloride (16 mmol) under an argon atmosphere in a baked-out Schlenk tube. The mixture was allowed to react for 18 hours at 40° C. For the work-up, the ionic phase was washed a number of times with toluene. The combined toluene extracts were filtered through a very short silica gel column (0.5 cm). The column was washed four times with 10 ml each time of toluene and the filtrates were evaporated.

Yield: 120 mg of 3,3'-bis2,5-dihydrofuranyl (87% of theory).

Example 10

Preparation of 1,3-di(3-trimethylsilyl-propen-1-yl) cyclopentane and 1-(3-trimethylsilyl-propen-1-yl)-3-vinyl-cyclopentane

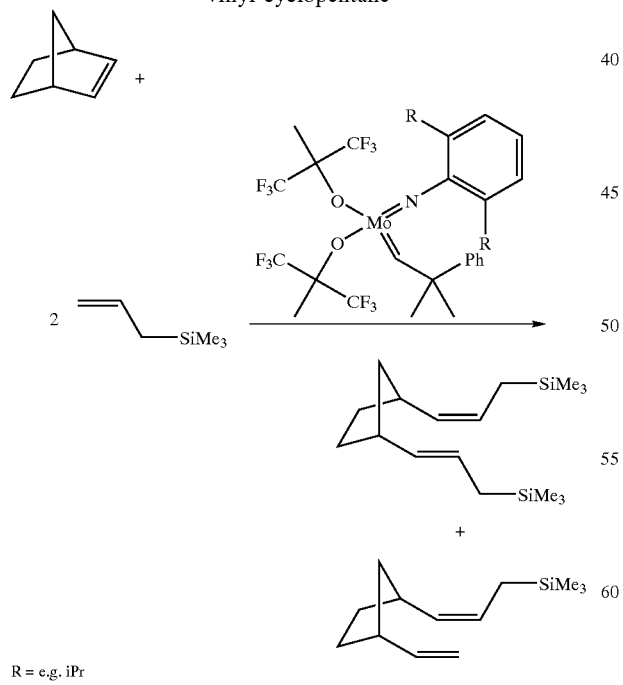

R = e.g. iPr 47 mg of norbornene (0.5 mmol) and 126 mg of allyltrimethylsilylsilane (1.1 mmol) were dissolved in a mixture of 289 mg (2 mmol) of 1methyl-3-ethylimidazolium chloride and 266 mg (2 mmol) of aluminium trichloride under an argon atmosphere. 10 mg (3 mol %) of the molybdenum catalyst shown above were subsequently added to this reaction mixture. The resulting mixture was covered with 3 ml of n-hexane and the mixture was allowed to react for one hour at room temperature.

After separating off the organic phase and extracting the ionic phase with n-hexane and then combining the organic extracts, the combined extracts were analysed by gas chromatography. Yield of disilylated product, viz. 1,3-di(3-trimethylsilylpropen-1-yl)cyclopentane: about 60% of theory; yield of monosilylated product, viz. 1-(3-trimethylsilyl-propen-1-yl)-3-vinyl-cyclopentane: about 20% of theory. In addition, polymeric products were found. No starting material could be detected.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a cyclic compound comprising subjecting a starting material in the presence of a catalyst component to metathesis reaction in the presence of an ionic liquid, and thereby forming the cyclic compound, wherein the starting material is α,ω-diene having the formula (I)

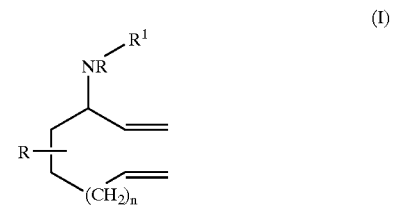

(I)

wherein n is 1, 2, 3 or 4,

R is hydrogen or an organic substituent selected from the group consisting of fused aryl groups, unfused aryl groups, alkyl groups, CN groups, and $COOR^2$ groups, $R^1$ is tert-butyl, $P(R)_2$, $P(R^2)_2$, COR, $SO_2PhR$, COOR or $CONRR^2$, $R^2$ is alkyl or phenyl, or R and $R^1$ together form

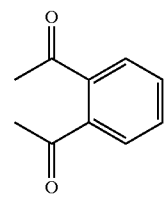

and wherein the α,ω-diene optionally bears at least one further substituent R in any other position with the exception of the α position, wherein the catalyst component is a ruthenium, an osmium, or a molybdenum homogenous catalyst or a heterogeneous catalyst selected from the group consisting of (I) ruthenium, osmium, or molybdenum carbenes, (ii) transition metal compounds that form transition metal carbenes under the reaction conditions, and (iii) transition metal salts in combination with an alkylating agent.

2. The process of claim 1, wherein n is 1 or 2.

3. The process of claim 1, wherein n is 1.

4. The process of claim 1, wherein the α,ω-diene is diallylamine or 3-amino-1,7-octadiene, or 1,7-octadiene, 10-undecenoyl-allylamide, 1,4-bis-oxypropen-2-yl-but-2-ine or buten-4-yl 10-undecenoate.

5. The process of claim 4, wherein the α,ω-diene is in N-carboxymethyl-protected form.

6. The process of claim 1, wherein the catalyst component is a compound of formula (III) or (IV):

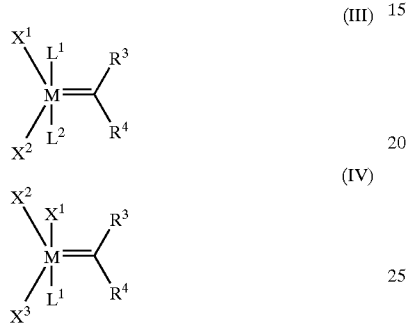

wherein M is ruthenium or osmium, and wherein $R^3$ to $R^7$ are radicals selected from the group consisting of hydrogen, $C_1$–$C_{20}$alkyl, $C_3$–$C_8$-cycloalkyl, $C_2$–$C_{20}$-alkenyl, $C_2$–$C_{20}$-alkinyl, $C_6$–$C_{18}$-aryl, $C_1$–$C_{20}$-carboxylate, $C_1$–$C_{20}$-alkoxy, $C_2$–$C_{20}$-alkenyloxy, $C_2$–$C_{20}$-alkinyloxy, $C_6$–$C_{18}$-aryloxy, $C_2$–$C_{20}$-alkoxycarbonyl, $C_1$–$C_{20}$-alkylthio, $C_1$–$C_{20}$-alkylsulfonyl and $C_1$–$C_{20}$-alkylsulfinyl, N-aryl; wherein in each case unsubstituted or substituted by $C_1$–$C_9$-alkyl, perfluoroalkyl, halogen, $C_1$–$C_5$-alkoxy or $C_6$–$C_{18}$-aryl; and wherein the radicals $R^3$ to $R^7$ may be linked to one another in cyclic compounds, $X^1$ to $X^3$ are anionic ligands are selected from the group consisting of $F^-$, $Cl^-$, $Br^-$, $CN^-$, $SCN^-$, $R^3O^-$, $R^3R^4N^-$, $(R^3–R^7)$-allyl$^-$, $(R^3–R^7)$-cyclopentadienyl$^-$, wherein the radicals $R^3$ to $R^7$ are as defined above, $L^1$ to $L^3$ are uncharged ligends are selected from the group consisting of CO, $CO_2$, $R^3NCO$, $R^3R^4C{=}CR^5R^8$, $R^3C{\equiv}CR^4$, $R^3R^4C{=}NR^5$, $R^3C{\equiv}N$, $R^3OR^4$, $R^3SR^4$, $NR^3R^4R^5$, $PR^3R^4R^5$, $AsR^3R^4R^5$, $SbR^3R^4R^5$, wherein the radicals $R^3$ to $R^5$ are as defined above.

7. The process of claim 6, wherein the catalyst component is a compound of the formula (III) and/or (IV), wherein $L^1$ and $L^2$ is $PR^3R^4R^5$.

8. The process of claim 7, wherein $R^3$, $R^4$, and $R^5$ are selected from the group consisting of aryl and alkyl groups.

9. The process of claim 7, wherein $R^3$, $R^4$, and $R^5$ are selected from the group consisting of secondary alkyl radicals and cycloalkyl radicals.

10. The process of claim 1, wherein the catalyst component is selected from one or more of the following compounds:

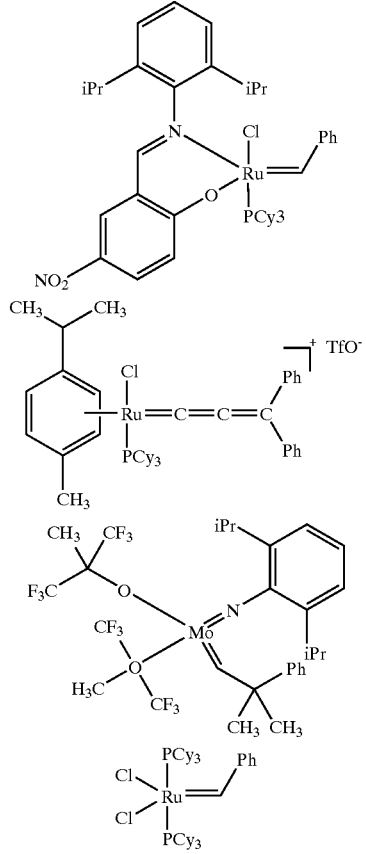

or combinations thereof.

11. The process of claim 1, wherein the ionic liquid is ammonium-hexafluorophosphate, ammonium tetrafluoroborate, ammonium tosylate, or ammonium hydrogen sulfate and salt mixtures comprising aluminium halides in combination with at least one quaternary ammonium halide and/or at least one quaternary phosphonium halide.

12. The process of claim 1, wherein the ionic liquid is pyridinium hexafluorophosphate, pyridinium tetrafluoroborate, pyridinium hydrogen sulfate, 1-methyl-3-butylimidazolium hexafluorophosphate or combinations of aluminum chloride with 1-methyl-3-butylimidazolium chloride, 1-methyl-3-ethylimidazolium chloride, N-butylpyridinium chloride and tetrabutylphosphonium halide.

* * * * *